United States Patent

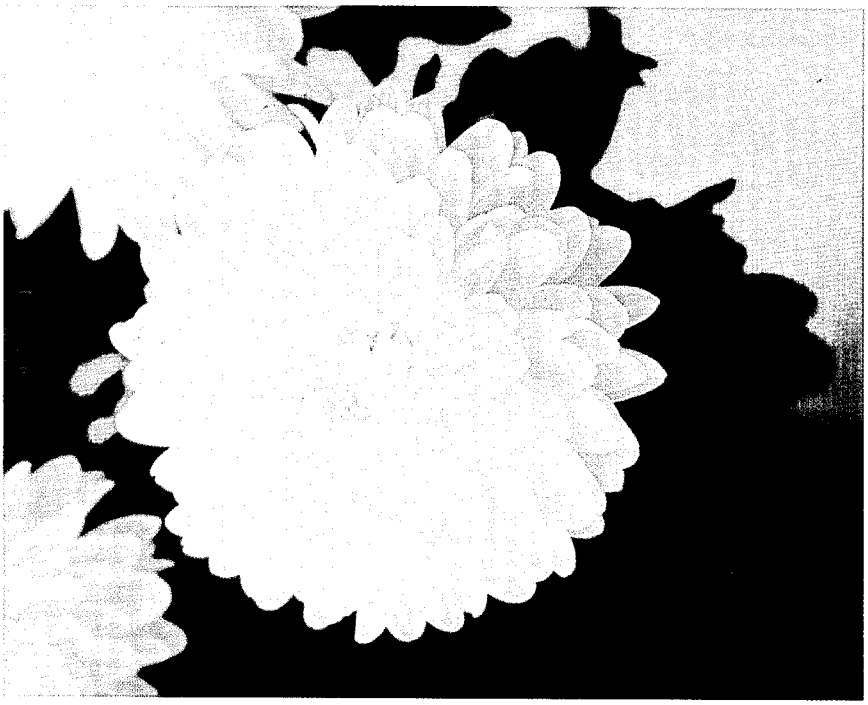
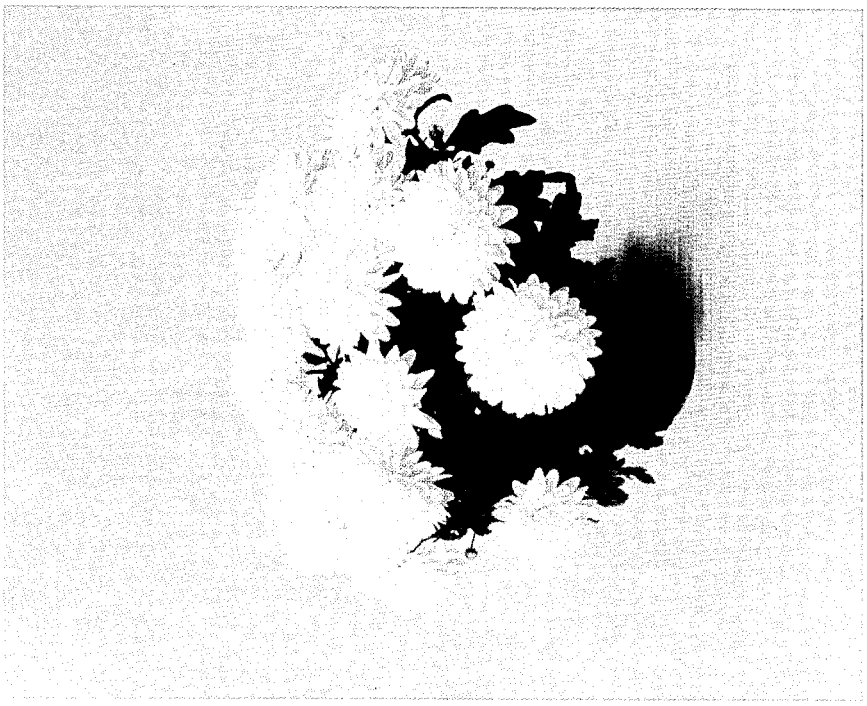

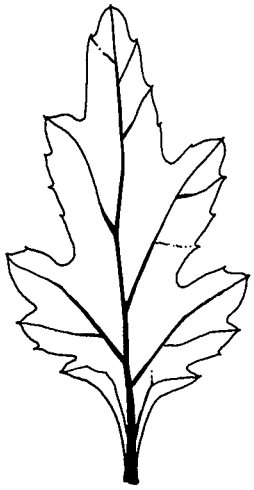
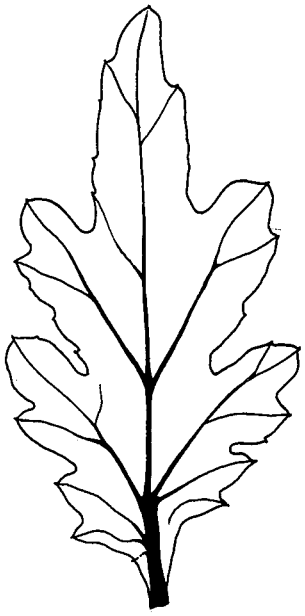
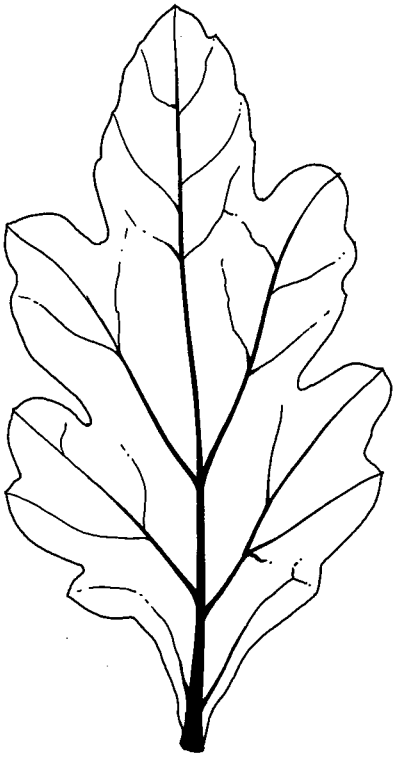

Plant Pat. 3,859

Patented Apr. 6, 1976

3,859

CHRYSANTHEMUM PLANT NAMED GOLDEN ST. MORITZ

Robert E. Danielson, West Chicago, Ill., assignor to Pan-American Plant Company, West Chicago, Ill.

Filed Mar. 24, 1975, Ser. No. 560,772

Int. Cl. A01h *5/00*

U.S. Cl. Plt.—78 1 Claim

ABSTRACT OF THE DISCLOSURE

A new and distinct variety of chrysanthemum plant of the greenhouse pot plant type particularly characterized by the deep yellow color of its relatively large blooms, which can be brought to flower the year around with appropriate photoperiod control, by its strong upright growth habit with abundant foliage, and by the excellent lasting quality of its flowers when in full bloom.

BACKGROUND OF THE NEW PLANT

My new variety of chrysanthemum plant was discovered by me in 1973, at West Chicago, Ill., as a sport of the variety "St. Moritz" (Plant Pat. 3,536) and because of its spectacular deep yellow color, this sport was taken for propagation and trial. Asexual propagation of this sport has been carried on by me and under my direction, by means of vegetative cuttings, though many generations, first at West Chicago, Ill., and later at both West Chicago, Ill. and at Cortez, Fla., and it has been found that while there is a slight color variation according to the time of year that the plant is brought to flower, regardless of whether propagated and grown in Florida or Illinois, the general and distinctive color effect is the same from generation to generation and appears to be firmly fixed.

DESCRIPTION OF THE DRAWINGS

This new variety of chrysanthemum plant is illustrated by the accompanying photographic drawing which in one view shows the form and color characteristics of a fully developed flower and in another view a typical potted plant display in full bloom, these views being in full color which has been reproduced as true as is reasonably possible by conventional commercial photographic procedures. Also shown, on page 2 of the drawings, are sketches of typical leaves of this new plant showing three stages of maturity, the upper sketch being the youngest leaf and the bottom sketch being of a mature leaf.

DESCRIPTION OF THE NEW PLANT

The following is a detailed description of my new chrysanthemum variety with color designations according to the Horticultural Colour Chart (HCC) and the RHS Colour Chart (RHS), each as published by The Royal Horticultural Society of London, England.

THE PLANT

Origin: Seedling.

Parentage: St. Moritz (Plant Pat. 3,536).

Classification:

*Botanic.*—*Chrysanthemum morifolium.*

*Commercial.*—Greenhouse pot plant.

Form: Perennial, herbaceous bush.

Height: 12 to 15 inches.

Growth: Terminal. Sturdy and upright with good strength and average vigor.

Branching: Normal for this type of plant.

Foliage: Quantity—abundant. 8 leaves on 6 inches of stem.

*Leaf size.*—Mature leaf—about 4 inches long and 2½ inches wide.

*Shape.*—Lobed-ovate with slightly serrated margins.

*Surface aspect.*—Canescent.

*Color.*—Upper side—Ivy Green (HCC) 0001060. Under side—Spinach Green (HCC) 0960/1.

*Venation.*—Pinnate.

*Petioles.*—1½ inches long.

THE BUD

Form: Semispherical.

Size: Large—⅝ inch deep and ⅝ inch in diameter.

Opening rate: The bud opens slowly.

Color:

*When phyllaries first divide.*—Yellow (RHS) 4B and 5C.

*When florets begin to unfurl.*—Yellow (RHS) 12A.

Phyllaries: Spear-shaped.

*Color.*—Inside—Spinach Green (HCC) 0960. Outside—Spinch Green (HCC) 0960.

*Surface aspect.*—Glaucous.

Peduncle: Length—1½ to 2¼ inches.

*Strength.*—Erect.

*Surface aspect.*—Glaucous.

THE FLOWER

Blooming period: Selective, the year round, with appropriate photoperiod control.

Response: 9 weeks.

Natural flowering season: The 10 day period of about October 29 to November 7.

Blooms: Flower type—decorative.

*Borne.*—A single head of many florets borne on a receptacle.

*Size.*—Large. Diameter—4½ to 5 inches. Depth—5 inches.

*Shape.*—Cup shaped when bloom first opens, becoming globular when fully opened.

*Florets.*—Very many in number. Form: Linear with obtuse and spooned apex. Texture: Firm. Appearance: Shiny.

*Peduncle.*—Sturdy and upright. Length: 1½ to 2¼ inches. Color: Spinch Green (HCC) 0960/2.

Flower color:

Outer florets:

| Bloom period | Upper side | Reverse side |
|---|---|---|
| April | Yellow (RHS) 9B; Canary Yellow (HCC) 2/1. | Yellow (RHS) 9C. Canary Yellow (HCC) 2/2. |
| July | Yellow (RHS) 5A | Yellow (RHS) 5C. |
| October | Yellow (RHS) 9A | Yellow (RHS) 8A or 9C. |
| November | do | Yellow (RHS) 12B. |

Inside florets:

| Bloom period | Upper side | Reverse side |
|---|---|---|
| April | Yellow (RHS) 9A; Canary Yellow (HCC) 2. | Yellow (RHS) 9C. Canary Yellow (HCC) 2/2. |
| July | Yellow (RHS) 6A | Yellow (RHS) 8A. |
| October | Yellow (RHS) 9A | Yellow (RHS) 7B. |
| November | Yellow (RHS) 12A | Yellow (RHS) 9A and 12A. |

Discoloration: Slight fade after full bloom.

Persistence: Florets hang on and dry.

Lasting quality: 3 weeks in full bloom.

REPRODUCTIVE ORGANS

Stamens:

Filaments.—¼ inch long. Color. Light Yellow.

*Anthers.*—None evident.

*Pollen.*—Color—Yellow.

Pistils: One for each ray floret.

*Style.*—5/16 inch long.

*Stigmas.*—Color—Yellow.

Ovaries: Inferior, bicarpellate.

This new chrysanthemum has substantially all of the favorable characteristics of its parent "St. Moritz" except color and in this respect, the new plant is especially unique in the deep yellow color of its blooms, and in the less reflexing of the outer ray florets. This new variety is thus a fine color companion for the other yellow varieties that are so popular in the marketplace.

I claim:

1. A new and distinctive variety of chrysanthemum plant of the greenhouse pot plant type substantially as herein shown and described, characterized particularly by the uniqueness of its deep yellow color when compared with its parent cultivar "St. Moritz" and by the less reflexing of the outer ray petals.

No references cited.

ROBERT E. BAGWILL, Primary Examiner